US008492408B2

(12) United States Patent
Larsen et al.

(10) Patent No.: US 8,492,408 B2
(45) Date of Patent: Jul. 23, 2013

(54) BENZIMIDAZOLE DERIVATIVES AND THEIR USE FOR MODULATING THE GABA$_A$ RECEPTOR COMPLEX

(75) Inventors: Janus S. Larsen, Holbæk (DK); Philip K. Ahring, Bagsværd (DK); Elsebet Østergaard Nielsen, København K (DK); Naheed Mirza, West Lothian (GB)

(73) Assignee: Aniona APS, Farum (DK)

( * ) Notice: Subject to any disclaimer, the term of this patent is extended or adjusted under 35 U.S.C. 154(b) by 173 days.

(21) Appl. No.: 13/129,066

(22) PCT Filed: Nov. 13, 2009

(86) PCT No.: PCT/EP2009/065125
§ 371 (c)(1),
(2), (4) Date: Jul. 11, 2011

(87) PCT Pub. No.: WO2010/055132
PCT Pub. Date: May 20, 2010

(65) Prior Publication Data
US 2011/0257230 A1    Oct. 20, 2011

Related U.S. Application Data

(60) Provisional application No. 61/114,949, filed on Nov. 14, 2008.

(30) Foreign Application Priority Data

Nov. 14, 2008 (DK) .................................. 2008 01588

(51) Int. Cl.
*A61K 31/4439*     (2006.01)
*C07D 401/14*      (2006.01)

(52) U.S. Cl.
USPC ............................................ 514/333; 546/256

(58) Field of Classification Search
USPC ........................................... 546/256; 514/333
See application file for complete search history.

(56) References Cited

U.S. PATENT DOCUMENTS

| 5,360,809 A | 11/1994 | Axelsson et al. |
| 5,554,630 A | 9/1996 | Teuber et al. |
| 5,554,632 A | 9/1996 | Teuber et al. |
| 7,902,230 B2 | 3/2011 | Larsen et al. |
| 2006/0069135 A1 | 3/2006 | Teuber et al. |

FOREIGN PATENT DOCUMENTS

| EP | 0 563 001 A1 | 9/1993 |
| EP | 0 616 807 B1 | 9/1994 |
| WO | WO 2004/087690 A2 | 10/2004 |
| WO | WO 2007/110374 A1 | 10/2007 |

OTHER PUBLICATIONS

International Search Report, dated Sep. 2, 2010, issued in PCT/EP2009/065125.
Mirza et al. "NS11394 [3'-[5-(1-Hydroxy-1-methyl-ethyl)-benzoimidazol-1-yl]-biphenyl-2-carbonitrile], a Unique Subtype-Selective GABAA Receptor Positive Allosteric Modulator: In Vitro Actions, Pharmacokinetic Properties and in Vivo Anxiolytic Efficacy", J. of Pharmacology and Experimental Therapeutics, 2008 vol. 327, No. 3, pp. 954-968, XP002565109.

*Primary Examiner* — Patricia L Morris
(74) *Attorney, Agent, or Firm* — Birch, Stewart, Kolasch & Birch, LLP

(57) ABSTRACT

The present application discloses novel benzimidazole derivatives and their use as modulators of the GABA$_A$ receptor complex. In other aspects the application discloses the use of these compounds, in a method for therapy and to pharmaceutical compositions comprising these compounds.

6 Claims, No Drawings

BENZIMIDAZOLE DERIVATIVES AND THEIR USE FOR MODULATING THE GABA$_A$ RECEPTOR COMPLEX

CROSS REFERENCE TO RELATED APPLICATIONS

This application is the National Phase of PCT/EP2009/065125 filed on Nov. 13, 2009 which claims priority under 35 U.S.C. 119(e) to U.S. Provisional Application No. 61/114,949 filed on Nov. 14, 2008 and under 35 U.S.C. 119(a) to Patent Application No. PA 2008 01588 filed in Denmark on Nov. 14, 2008, all of which are hereby expressly incorporated by reference into the present application.

TECHNICAL FIELD

This invention relates to novel benzimidazole derivatives, pharmaceutical compositions containing these compounds, and methods of treatment therewith.

The compounds of the invention are useful in the treatment of central nervous system diseases and disorders which are responsive to modulation of the GABA$_A$ receptor complex, and in particular for combating anxiety and related diseases.

BACKGROUND ART

The modulatory sites on the GABA$_A$ receptor complex, such as for example the benzodiazepine binding site, are the target for anxiolytic drugs, such as the classical anxiolytic benzodiazepines. However, they are associated with a number of undesirable features.

Multiple isoforms of the GABA$_A$ receptor exist; each receptor is a pentameric complex comprising subunits drawn from $\alpha_{1-6}$, $\beta_{1-3}$, $\gamma_{1-3}$, $\delta$, $\epsilon$, and $\theta$ subunit isoforms. The classical anxiolytic benzodiazepines show no subtype selectivity. It has been suggested that one of the key elements in the disadvantages of the classical benzodiazepanes (such as sedation, dependency, and cognitive impairment) is relates to the $\alpha 1$ subunit of the GABA$_A$ receptors. Thus compounds with selectivity for the $\alpha 2$ and/or $\alpha 3$ subunits over the $\alpha 1$ subunit are expected to have an improved side effect profile.

Thus, there is still a strong need for compounds with an optimised pharmacological profile. Furthermore, there is a strong need to find effective compounds without unwanted side effects associated with older compounds.

SUMMARY OF THE INVENTION

In its first aspect, the invention provides a compound of Formula I:

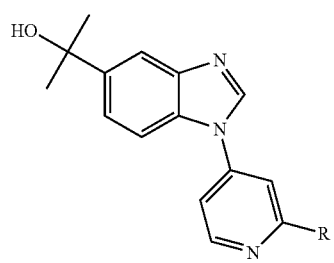

(I)

or an N-oxide thereof, any of its stereoisomers or any mixture of its stereoisomers, or a pharmaceutically acceptable salt thereof, wherein R is defined as below.

In its second aspect, the invention provides a pharmaceutical composition, comprising a therapeutically effective amount of a compound of the invention, or an N-oxide thereof, any of its isomers or any mixture of its isomers, or a pharmaceutically acceptable salt thereof, together with at least one pharmaceutically acceptable carrier, excipient or diluent.

In a further aspect, the invention provides the use of a compound of the invention, or an N-oxide thereof, any of its stereoisomers or any mixture of its stereoisomers, or a pharmaceutically acceptable salt thereof, for the manufacture of a pharmaceutical composition for the treatment, prevention or alleviation of a disease or a disorder or a condition of a mammal, including a human, which disease, disorder or condition is responsive to modulation of the GABA$_A$ receptor complex.

In a still further aspect, the invention relates to a method for treatment, prevention or alleviation of a disease or a disorder or a condition of a living animal body, including a human, which disorder, disease or condition is responsive to modulation of the GABA$_A$ receptor complex, which method comprises the step of administering to such a living animal body in need thereof a therapeutically effective amount of a compound of the invention, or an N-oxide thereof, any of its stereoisomers or any mixture of its stereoisomers, or a pharmaceutically acceptable salt thereof.

Other objects of the invention will be apparent to the person skilled in the art from the following detailed description and examples.

DETAILED DISCLOSURE OF THE INVENTION

Substituted Benzimidazole Derivatives

In its first aspect the present invention provides a compound of general formula I:

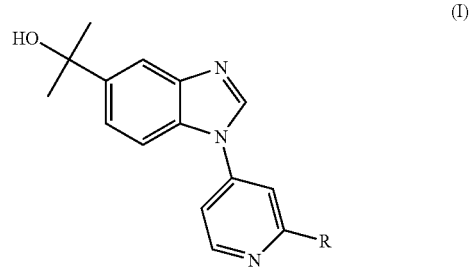

(I)

or an N-oxide thereof, any of its isomers or any mixture of its isomers,
or a pharmaceutically acceptable salt thereof;
wherein R represents a pyridyl group;
  which pyridyl group is optionally substituted with one or more substituents independently selected from the group consisting of:
    halo, trifluoromethyl, trifluoromethoxy, cyano, nitro, alkyl, hydroxy, hydroxyalkyl and alkoxy.

In one embodiment of the compound of general formula (I), R represents a pyridyl group, which pyridyl group is substituted with one or more substituents independently selected from the group consisting of: halo, cyano and alkoxy.

In a further embodiment of the compound of general formula (I), R represents

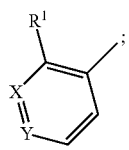

wherein one of X and Y represents N and the other of X and Y represents CH; and
$R^1$ represents halo, trifluoromethyl, trifluoromethoxy, cyano, nitro, alkyl, hydroxy, hydroxyalkyl or alkoxy.

In a further embodiment, $R^1$ represents halo, such as fluoro or chloro. In a further embodiment, $R^1$ represents cyano. In a still further embodiment, $R^1$ represents alkoxy, such as methoxy.

In a further embodiment, X represents N and Y represents CH.

In a still further embodiment, X represents CH and Y represents N.

In a further embodiment of the compound of general formula (I), R represents 2-methoxy-pyridin-3-yl, 2-chloro-pyridin-3-yl, 3-fluoro-pyridin-4-yl or 3-cyano-pyridin-4-yl.

In a further embodiment the compound of the invention is
2-[1-(2'-Methoxy-[2,3']bipyridinyl-4-yl)-1H-benzoimidazol-5-yl]-propan-2-ol;
2-[1-(2'-Chloro-[2,3']bipyridinyl-4-yl)-1H-benzoimidazol-5-yl]-propan-2-ol;
2-[1-(3'-Fluoro-[2,4']bipyridinyl-4-yl)-1H-benzoimidazol-5-yl]-propan-2-ol;
4-[5-(1-Hydroxy-1-methyl-ethyl)-benzoimidazol-1-yl]-[2,4']bipyridinyl-3'-carbonitrile;
or an N-oxide thereof, any of its stereoisomers or any mixture of its stereoisomers,
or a pharmaceutically acceptable salt thereof.

Any combination of two or more of the embodiments as described above is considered within the scope of the present invention.

DEFINITION OF TERMS

As used throughout the present specification and appended claims, the following terms have the indicated meaning:

The term "alkyl" as used herein means a saturated, branched or straight hydrocarbon group having from 1-6 carbon atoms, e.g. $C_{1-3}$-alkyl, $C_{1-4}$-alkyl, $C_{1-6}$-alkyl, $C_{2-6}$-alkyl, $C_{3-6}$-alkyl, and the like. Representative examples are methyl, ethyl, propyl (e.g. prop-1-yl, prop-2-yl (or iso-propyl)), butyl (e.g. 2-methylprop-2-yl (or tert-butyl), but-1-yl, but-2-yl), pentyl (e.g. pent-1-yl, pent-2-yl, pent-3-yl), 2-methylbut-1-yl, 3-methylbut-1-yl, hexyl (e.g. hex-1-yl), heptyl (e.g. hept-1-yl), octyl (e.g. oct-1-yl), nonyl (e.g. non-1-yl), and the like.

The term "halo" or "halogen" means fluorine, chlorine, bromine or iodine.

The term "cyano" shall mean the radical —CN.
The term "nitro" shall mean the radical —$NO_2$.
The term "hydroxy" shall mean the radical —OH.
The term "hydroxyalkyl" as used herein refers to $C_{1-6}$-alkyl substituted one or more times at any carbon atom(s) with hydroxyl. Representative examples are hydroxymethyl, hydoxyethyl (e.g. 1-hydroxyethyl, 2-hydroxyethyl) and the like.

The term "alkoxy" as used herein refers to the radical —O—$C_{1-6}$-alkyl. Representative examples are methoxy, ethoxy, propoxy (e.g. 1-propoxy, 2-propoxy), butoxy (e.g. 1-butoxy, 2-butoxy, 2-methyl-2-propoxy), pentoxy (1-pentoxy, 2-pentoxy), hexoxy (1-hexoxy, 3-hexoxy), and the like.

The term "optionally substituted" as used herein means that the groups in question are either unsubstituted or substituted with one or more of the substituents specified. When the group(s) in question is/are substituted with more than one substituent the substituents may be the same or different.

Certain of the defined terms may occur more than once in the structural formulae, and upon such occurrence each term shall be defined independently of the other.

The term "treatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

The terms "disease", "condition" and "disorder" as used herein are used interchangeably to specify a state of a patient which is not the normal physiological state of man.

The term "medicament" as used herein means a pharmaceutical composition suitable for administration of the pharmaceutically active compound to a patient.

The term "pharmaceutically acceptable" as used herein means suited for normal pharmaceutical applications, i.e. giving rise to no adverse events in patients etc.

The term "effective amount" as used herein means a dosage which is sufficient in order for the treatment of the patient to be effective compared with no treatment.

The term "therapeutically effective amount" of a compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

Pharmaceutically Acceptable Salts

The compounds of the invention may be provided in any form suitable for the intended administration. Suitable forms include pharmaceutically (i.e. physiologically) acceptable salts, and pre- or prodrug forms of the compounds of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycollate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a compound of the invention and its pharmaceutically acceptable acid addition salt.

Examples of pharmaceutically acceptable cationic salts of a compound of the invention include, without limitation, the sodium, the potassium, the calcium, the magnesium, the zinc, the aluminium, the lithium, the choline, the lysinium, and the ammonium salt, and the like, of a compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the compound of the invention include examples of suitable prodrugs of the substances according to the invention including compounds modified at one or more reactive or derivatizable groups of the parent compound. Of particular interest are compounds modified at a carboxyl group, a hydroxyl group, or an amino group. Examples of suitable derivatives are esters or amides.

The compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

It will be appreciated by those skilled in the art that the compounds of the present invention may exist in different stereoisomeric forms—including enantiomers, diastereomers and cis-trans-isomers.

The invention includes all such stereoisomers and any mixtures thereof including racemic mixtures.

Methods for the resolution of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

Optical active compounds can also be prepared from optical active starting materials.

N-Oxides

In the context of this invention an N-oxide designates an oxide derivative of a tertiary amine, including a nitrogen atom of an aromatic N-heterocyclic compound, a non-aromatic N-heterocyclic compounds, a trialkylamine and a trialkenylamine. For example, the N-oxide of a compound containing a pyridyl may be the 1-oxy-pyridin-2, -3 or -4-yl derivative.

N-oxides of the compounds of the invention may be prepared by oxidation of the corresponding nitrogen base using a conventional oxidizing agent such as hydrogen peroxide in the presence of an acid such as acetic acid at an elevated temperature, or by reaction with a peracid such as peracetic acid in a suitable solvent, e.g. dichloromethane, ethyl acetate or methyl acetate, or in chloroform or dichloromethane with 3-chloroperoxybenzoic acid.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radionuclide as a label. Positron emitting radionuclides are all candidates for usage. In the context of this invention the radionuclide is preferably selected from $^2$H (deuterium), $^3$H (tritium), $^{11}$C, $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

The compounds of this invention may exist in unsolvated as well as in solvated forms with pharmaceutically acceptable solvents such as water, ethanol and the like. In general, the solvated forms are considered equivalent to the unsolvated forms for the purposes of this invention.

Biological Activity

Compounds of the invention are capable of modulating the $GABA_A$ receptor complex. They may be tested for their ability to bind to the $GABA_A$ receptor complex, including specific subunits thereof.

The compounds of the present invention, being ligands for the benzodiazepine binding site on $GABA_A$ receptors, are therefore of use in the treatment and/or prevention of a variety of disorders of and outside the central nervous system. Thus in further aspect, the compounds of the invention are considered useful for the treatment, prevention or alleviation of a disease, disorder or condition responsive to modulation of the $GABA_A$ receptor complex, in particular in the central nervous system. In a further embodiment, the compounds of the invention are ligands of the $GABA_A$ receptor complex outside the central nervous system.

In one embodiment, the compounds of the invention are considered useful for the treatment, prevention or alleviation of anxiety disorders, panic disorder with or without agoraphobia, agoraphobia without history of panic disorder, phobia, animal phobia, social phobia, obsessive-compulsive disorder (OCD), generalized anxiety disorder, substance-induced anxiety disorder; stress disorders, post-traumatic stress disorder, separation anxiety disorder, acute stress disorder, sleep disorder, memory disorder, neurosis, convulsive disorder, epilepsy, seizures, convulsions, febrile convulsions in children, mood disorder, depressive disorder, bipolar disorder, depression, major depressive disorder, single-episode major depressive disorder, recurrent major depressive disorder, dysthymic disorder, bipolar disorder, manic disorder, bipolar I manic disorder, bipolar II manic disorder, cyclothymic disorder, psychotic disorder, schizophrenia, cognitive disorder, learning deficit, memory deficits and dysfunction, dementia, attention deficit, attention deficit hyperactivity disorder (ADHD), Down's syndrome, Tourette's syndrome, Alzheimer's disease, Parkinson's disease, Huntington's disease, Pick's disease, Creutzfeldt-Jakob disease, cognitive impairment, cognition deficits in schizophrenia, tichotillamania, stuttering, general tic disorders, muscle tension disorders, cerebral ischemia, stroke, head trauma, neurodegeneration arising from cerebral ischemia, pain consisting of, acute pain, chronic pain, mild pain, moderate or severe pain, postoperative pain, neuropathic pain, central neuropathic pain, pain related to diabetic neuropathy, to postherpetic neuralgia, to peripheral nerve injury, to phantom limb pain, to fibromyalgia, to chronic regional pain syndrome, somatic pain, visceral pain or cutaneous pain, pain caused by inflammation or by infection, pain related to osteoarthritis, rheumatoid arthritis, neuronal hyperexcitability disorders, peripheral nerve hyperexcitability, chronic headache, migraine, migraine-related disorders, tension-type headache, nociception emesis, acute, delayed and anticipatory emesis, particular emesis induced by chemotherapy or radiation, motion sickness, postoperative nausea, vomiting, eating disorders, feeding disorders, obesity, weight gain, anorexia nervosa, bulimia nervosa, orthorexia nervosa, bringe eating disorder (BED), premenstrual syndrome, neuralgia, trigeminal neuralgia, muscle spasm, spasticity, e.g. in paraplegic patients, the effects of substance abuse or dependency, alcohol withdrawal, tinnitus, disorder of circadian rhythm, disorders of circadian rhythm in subjects suffering from the effects of jet lag or shift work, diabetes, type 1 diabetes, type 2 diabetes, hyperinsulinemia, dyslipidemia, hyperlipidemia, inflammatory disease or auto immune disorder.

In another embodiment, the compounds are considered useful for the treatment or alleviation of anxiety, e.g. anxiety disorders, panic disorder with or without agoraphobia, agoraphobia without history of panic disorder, phobia, animal phobia, social phobia, obsessive-compulsive disorder, generalized anxiety disorder, substance-induced anxiety disorder; stress disorders, post-traumatic stress disorder, separation anxiety disorder, acute stress disorder or, sleep disorder. In another embodiment, the compounds are considered useful for the treatment or alleviation of anxiety. In another embodiment, the compounds are considered useful for the treatment or alleviation of pain, e.g. acute pain, chronic pain, mild pain, moderate or severe pain, neuropathic pain, central pain, pain related to diabetic neuropathy, to postherpetic neuralgia, to peripheral nerve injury, somatic pain, visceral pain or cutaneous pain, pain caused by inflammation or by infection, postoperative pain, phantom limb pain, neuronal hyperexcitability disorders, peripheral nerve hyperexcitability, chronic headache, migraine, migraine-related disorders or tension-type headache. In another embodiment, the compounds are considered useful for the treatment or alleviation of pain. In another embodiment, the compounds are considered useful for the treatment or alleviation of schizophrenia, cognitive disorder, learning deficit, memory deficits and dysfunction, dementia, attention deficit, attention deficit hyperactivity disorder (ADHD), Down's syndrome, Tourette's syndrome, Alzheimer's disease, Parkinson's disease, Huntington's disease, Pick's disease, Creutzfeldt-Jakob disease, cognitive impairment, cognition deficits in schizophrenia, tichotillamania, stuttering, general tic disorders, muscle tension disorders, cerebral ischemia, stroke, head trauma, neurodegeneration arising from cerebral ischemia. In another embodiment, the compounds are considered useful for the treatment or alleviation of schizophrenia.

Further, the compounds of the invention may be useful as radioligands in assays for detecting compounds capable of binding to the human $GABA_A$ receptor.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Pharmaceutical Compositions

In another aspect the invention provides novel pharmaceutical compositions comprising a therapeutically effective amount of the compound of the invention.

While a compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the compound of the invention, or a pharmaceutically acceptable salt or derivative thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The compound of the present invention can be administered in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from a compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, cellulose, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

In one embodiment, the invention provides tablets or capsules for oral administration.

In another embodiment, the invention provides liquids for intravenous administration and continuous infusion.

Further details on techniques for formulation and administration may be found in the latest edition of *Remington's Pharmaceutical Sciences* (Maack Publishing Co., Easton, Pa.).

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 μg/kg i.v. and 1 μg/kg p.o. The upper limit of the dosage range is presently considered to be about 10 mg/kg i.v. and 100 mg/kg p.o. Preferred ranges are from about 0.1 μg/kg to about 10 mg/kg/day i.v., and from about 1 μg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to modulation of the $GABA_A$ receptor complex, and which method comprises administering to such a living animal body, including a human, in need thereof an effective amount of a compound of the invention.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

General

All reactions involving air sensitive reagents or intermediates were performed under nitrogen and in anhydrous solvents. Magnesium sulphate or sodium sulphate was used as drying agent in the workup-procedures and solvents were evaporated under reduced pressure.

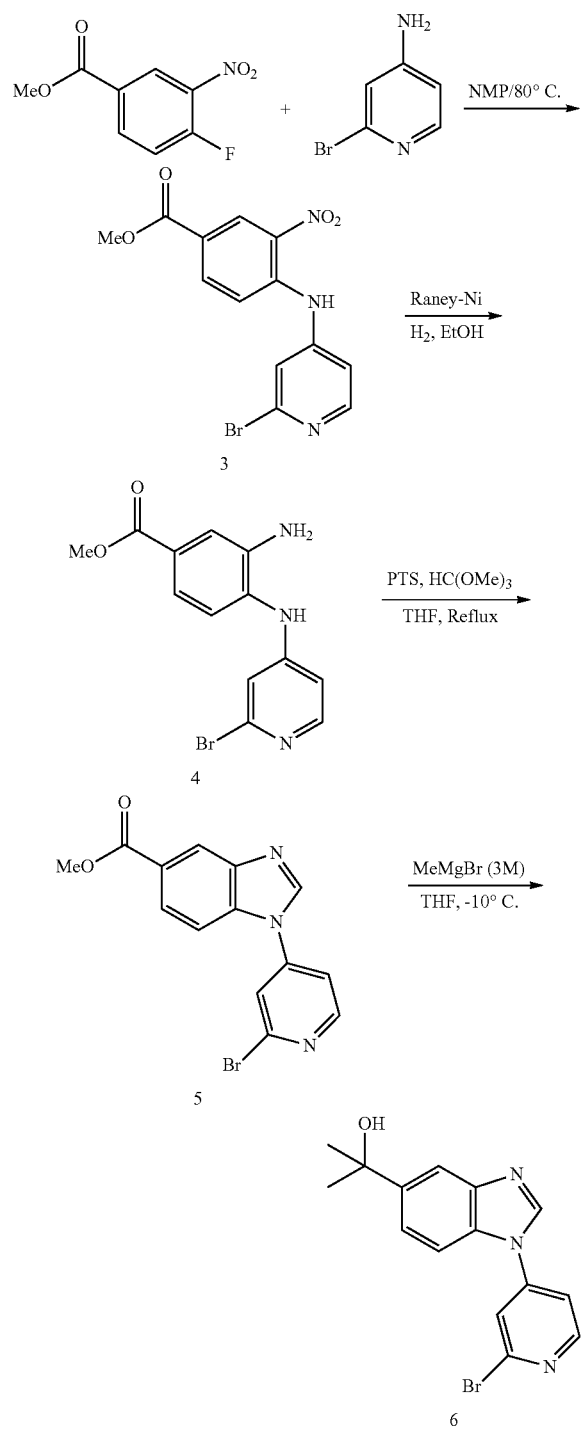

Synthesis of 4-(2-bromo-pyridin-4-ylamino)-3-nitro-benzoic Acid Methyl Ester (3)

2-Bromo-pyridin-4-ylamine 2 (4.3 g; 25 mmol) and NaH 60% (1.5 g; 37 mmol) was at 0° C. stirred for 1 h in dry THF (50 ml) and then a solution of 4-Fluoro-3-nitro-benzoic acid methyl ester 1 (5 g; 25 mmol) in dry THF (50 ml) was addeddrop. The resulting cold solution was allowed to reach RT and stirred overnight for completion of the reaction. LCMS showed complete conversion to product and the reaction was quenched by addition of iPrOH and H$_2$O. A precipitate was formed and this was filtered off, dried under educed pressure to obtain 3 as a yellow solid (7.5 g). Yield 85%. The product identity was confirmed by NMR and LCMS and taken for the next step.

Synthesis of 3-amino-4-(2-bromo-pyridin-4-ylamino)-benzoic Acid Methyl Ester (4)

4-(2-Bromo-pyridin-4-ylamino)-3-nitro-benzoic acid methyl ester 3 (6 g; 17 mmol) was dissolved in MeOH (200 ml) and Raney-nickel (0.6 g; 4.5 mmol) was added and subsequently hydrogenated under an atmosphere of H$_2$ for 3 h. LCMS showed full conversion and the reaction mixture was filtered through a bed of Celite to remove the catalyst. Thorough washing with MeOH followed by evaporation of the solvent under educed pressure gave 4 as a brown solid. Yield 3.2 g; 60%. The product identity was confirmed by NMR and LCMS and taken for the next step.

Synthesis 1-(2-bromo-pyridin-4-yl)-1H-benzoimidazole-5-carboxylic Acid methyl ester (5)

3-Amino-4-(2-bromo-pyridin-4-ylamino)-benzoic acid methyl ester 4 (3 g; 9.3 mmol) was dissolved in 50 ml dry THF and added trimethyl orthoformate (1.4 ml; 13.9 mmol) and p-toluenesulphonic acid (1 g), the reaction mixture was heated to 60° C. for 6 h. LCMS showed almost complete conversion and the reaction was quenched with sodium bicarbonate and extracted with EtOAc (500 ml*3). The organic layer was washed with water and brine. Finally it was dried over sodium sulphate and concentrated in vacuo to give the expected product 5. The compound was pure enough for progress into the next step as seen by NMR and HPLC.

Synthesis of 2-[1-(2-bromo-pyridin-4-yl)-1H-benzoimidazol-5-yl]-propan-2-ol (6)

1-(2-Bromo-pyridin-4-yl)-1H-benzoimidazole-5-carboxylic acid methyl ester 5 (32 g; 96 mmol) was dissolved in 550 ml dry THF and cooled to −10° C. To this solution was added dropwise MeMgBr (3 M, 128 ml; 385 mmol), after end of addition the reaction mixture was allowed to reach RT and stirred at ambient temperature overnight. The reaction was quenched by addition of NH$_4$Cl$_{(sat)}$ and subsequently extracted with EtOAc. The organic layer was washed with water and brine and dried over sodium sulphate followed by concentration in vacuo to give 32 g of an impure solid. Purification by flash chromatography (MeOH/CHCl$_3$) gave the pure product after concentration of desired fractions 7.2 g. Yield 22.5%. The compound was pure enough for progress into the next step as seen by NMR and HPLC.

Method A: General Procedure for Suzuki Coupling

To a solution of compound 6 (1 eq.) and heteroarylboronic acid (1.5 eq.) or the corresponding boronic acid esters, was dissolved/suspended in DME/H$_2$O/1,3-propanediol or Dioxane/H$_2$O/EtOH and Na$_2$CO$_3$ (~3 eq.) was added. The catalyst (Ph$_3$P)$_2$PdCl$_2$ (5 mol %) or (Ph$_3$P)$_4$Pd (5 mol %) was added and the reaction mixture was stirred at 90° C. overnight. The reaction mixture was cooled to RT, diluted with water, extracted with ethylacetate, dried over Na$_2$SO$_4$ and concentrated under reduced pressure. The crude product was purified by silica gel column chromatography using either ethylacetate in hexane (gradient) or CH$_2$Cl$_2$/MeOH/NH$_{4(aq)}$. (95:5: 0.1%) as mobile phase to give target compounds 7a-7e.

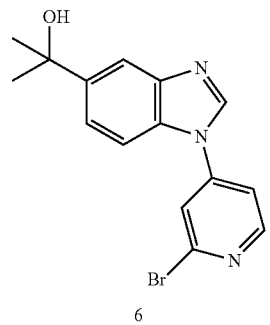

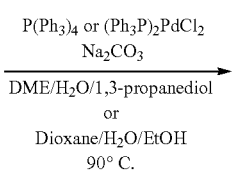

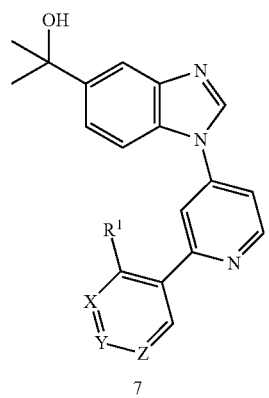

The following compounds were be prepared using the above mentioned protocols for Suzuki coupling.

| Compound | Starting Material | R$^1$ | X | Y | Z |
|---|---|---|---|---|---|
| 7a | 6 | OMe | N | C—H | C—H |
| 7b | 6 | Cl | N | C—H | C—H |
| 7c | 6 | F | C—H | N | C—H |
| 7d | 6 | CN | C—H | N | C—H |

2-[1-(2'-Methoxy-[2,3']bipyridinyl-4-yl)-1H-benzoimidazol-5-yl]-propan-2-ol 7a

LC-ESI-HRMS of [M+H]+ shows 361.1665 Da. Calc. 361.165906 Da, dev. 1.6 ppm

2-[1-(2'-Chloro-[2,3']bipyridinyl-4-yl)-1H-benzoimidazol-5-yl]-propan-2-ol 7b

LC-ESI-HRMS of [M+H]+ shows 365.1172 Da. Calc. 365.116369 Da, dev. 2.3 ppm

2-[1-(3'-Fluoro-[2,4']bipyridinyl-4-yl)-1H-benzoimidazol-5-yl]-propan-2-ol 7c

LC-ESI-HRMS of [M+H]+ shows 349.1471 Da. Calc. 349.145919 Da, dev. 3.4 ppm

4-[5-(1-Hydroxy-1-methyl-ethyl)-benzoimidazol-1-yl]-[2,4']bipyridinyl-3'-carbonitrile 7d LC-ESI-HRMS of [M+H]+ shows 356.1517 Da. Calc. 356.15059 Da, dev. 3.1 ppm Test Methods The compounds of the present invention may be tested for their in vitro actions, pharmacokinetic properties and in vivo actions using standard pharmacological procedures in cell cultures or experimental animals, such as those described in Mirza N R et al, NS11394 ([3'-[5-(1-Hydroxy-1-methyl-ethyl)-benzoimidazol-1-yl]-biphenyl-2-carbonitrile]), a unique subtype-selective $GABA_A$ receptor positive modulator: In vitro actions, pharmacokinetic properties and in-vivo anxiolytic efficacy; *Journal of Pharmacology And Experimental Therapeutics Fast Forward*; first published on Sep. 12, 2008; DOI: 10.1124/j pet.108.138859.

Test Method 1

In Vitro Inhibition of $^3$H-Flunitrazepam ($^3$H-FNM) Binding

The GABA recognition site and the benzodiazepine modulatory unit can selectively be labelled with $^3$H-flunitrazepam.

Tissue Preparation

Preparations are performed at 0-4° C. unless otherwise indicated. Cerebral cortex from male Wistar rats (150-200 g) is homogenised for 5-10 sec in 20 ml Tris-HCl (30 mM, pH 7.4) using an Ultra-Turrax homogeniser. The suspension is centrifuged at 27,000×g for 15 min and the pellet is washed three times with buffer (centrifuged at 27,000×g for 10 min). The washed pellet is homogenized in 20 ml of buffer and incubated on a water bath (37° C.) for 30 min to remove endogenous GABA and then centrifuged for 10 min at 27,000×g. The pellet is then homogenized in buffer and centrifuged for 10 min at 27,000×g. The final pellet is resuspended in 30 ml buffer and the preparation is frozen and stored at −20° C.

Assay

The membrane preparation is thawed and centrifuged at 2° C. for 10 min at 27,000×g. The pellet is washed twice with 20 ml 50 mM Tris-citrate, pH 7.1 using an Ultra-Turrax homogeniser and centrifuged for 10 min at 27,000×g. The final pellet is resuspended in 50 mM Tris-citrate, pH 7.1 (500 ml buffer per g of original tissue), and then used for binding assays. Aliquots of 0.5 ml tissue are added to 25 µl of test solution and 25 µl of $^3$H-FNM (1 nM, final concentration), mixed and incubated for 40 min at 2° C. Non-specific binding is determined using Clonazepam (1 µM, final concentration). After incubation the samples are added 5 ml of ice-cold buffer and poured directly onto Whatman GF/C glass fibre filters under suction and immediately washed with 5 ml ice-cold buffer. The amount of radioactivity on the filters is determined by conventional liquid scintillation counting. Specific binding is total binding minus non-specific binding.

Results 25-75% inhibition of specific binding must be obtained, before calculation of an $IC_{50}$.

The test value will be given as $IC_{50}$ (the concentration (µM) of the test substance which inhibits the specific binding of $^3$H-FNM by 50%).

$$IC_{50} = \text{(applied test substance concentration, } \mu M) \times \frac{1}{\left(\frac{C_o}{C_x}-1\right)}$$

where $C_o$ is specific binding in control assays, and $C_x$ is the specific binding in the test assay.

(The calculations assume normal mass-action kinetics).

Test results from these experiments with a number of compounds of the invention are shown in Table 1 below.

TABLE 1

| Test compound | In vitro binding $IC_{50}$ (µM) |
|---|---|
| 7a | 0.0012 |
| 7b | 0.038 |
| 7c | 0.0075 |
| 7d | 0.026 |

From the foregoing it will be appreciated that, although specific embodiments of the invention have been described herein for purposes of illustration, various modifications may be made without deviating from the spirit and scope of the invention. Accordingly, the invention is not to be limited as by the appended claims.

The features disclosed in the foregoing description, in the claims and/or in the accompanying drawings, may both separately and in any combination thereof, be material for realising the invention in diverse forms thereof.

The invention claimed is:

1. A compound of general formula I:

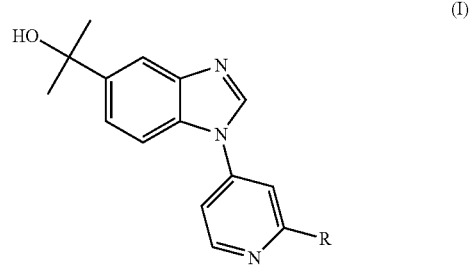

(I)

or an N-oxide thereof, any of its stereoisomers or any mixture of its stereoisomers, or a pharmaceutically acceptable salt thereof, wherein R represents a pyridyl group; which pyridyl group is optionally substituted with one or more substituents independently selected from the group consisting of: halo, trifluoromethyl, trifluoromethoxy, cyano, nitro, alkyl, hydroxy, hydroxyalkyl and alkoxy.

2. The compound according to claim 1, an N-oxide thereof, any of its stereoisomers or any mixture of its stereoisomers, or a pharmaceutically acceptable salt thereof, wherein R represents

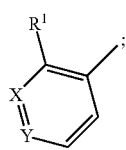

wherein one of X and Y represents N and the other of X and Y represents CH; and R¹ represents halo, trifluoromethyl, trifluoromethoxy, cyano, nitro, alkyl, hydroxy, hydroxyalkyl or alkoxy.

3. The compound according to claim 2, an N-oxide thereof, any of its stereoisomers or any mixture of its stereoisomers, or a pharmaceutically acceptable salt thereof, wherein X represents N and Y represents CH, and R¹ represents halo or alkoxy.

4. The compound of claim 1, which is
2-[1-(2'-Methoxy-[2,3']bipyridinyl-4-yl)-1H-benzoimidazol-5-yl]-propan-2-ol;
2-[1-(2'-Chloro-[2,3']bipyridinyl-4-yl)-1H-benzoimidazol-5-yl]-propan-2-ol;
2-[1-(3'-Fluoro-[2,4']bipyridinyl-4-yl)-1H-benzoimidazol-5-yl]-propan-2-ol;
4-[5-(1-Hydroxy-1-methyl-ethyl)-benzoimidazol-1-yl]-[2,4']bipyridinyl-3'-carbonitrile;
or an N-oxide thereof, any of its stereoisomers or any mixture of its stereoisomers, or a pharmaceutically acceptable salt thereof.

5. A pharmaceutical composition, comprising a therapeutically effective amount of a compound of claim 1, or an N-oxide thereof, any of its stereoisomers or any mixture of its stereoisomers, or a pharmaceutically acceptable salt thereof, together with at least one pharmaceutically acceptable carrier, excipient or diluent.

6. The compound of claim 1, which is
2-[1-(2'-Chloro-[2,3']bipyridinyl-4-yl)-1H-benzoimidazol-5-yl]-propan-2-ol;
or an N-oxide thereof, any of its stereoisomers or any mixture of its stereoisomers, or a pharmaceutically acceptable salt thereof.

* * * * *